(12) United States Patent
Ninomiya

(10) Patent No.: US 7,704,283 B2
(45) Date of Patent: Apr. 27, 2010

(54) PROSTHETIC LEG

(75) Inventor: Makoto Ninomiya, Nagasaki (JP)

(73) Assignees: Nagasaki Kanae Co., Nagasaki-shi (JP); Imasen Engineering Corporation, Inuyama (JP)

( * ) Notice: Subject to any disclaimer, the term of this patent is extended or adjusted under 35 U.S.C. 154(b) by 230 days.

(21) Appl. No.: 11/898,428

(22) Filed: Sep. 12, 2007

(65) Prior Publication Data
US 2008/0228287 A1 Sep. 18, 2008

(30) Foreign Application Priority Data
Mar. 13, 2007 (JP) .............................. 2007-063154

(51) Int. Cl.
*A61F 2/64* (2006.01)
*A61F 2/74* (2006.01)
(52) U.S. Cl. .............................. 623/37; 623/27; 623/26; 623/40; 623/44
(58) Field of Classification Search .............. 623/26–65
See application file for complete search history.

(56) References Cited

U.S. PATENT DOCUMENTS

| | | | | |
|---|---|---|---|---|
| 5,376,137 | A * | 12/1994 | Shorter et al. ................. | 623/44 |
| 6,517,585 | B1 * | 2/2003 | Zahedi et al. ................. | 623/24 |
| 6,613,097 | B1 * | 9/2003 | Cooper ......................... | 623/44 |
| 2004/0083007 | A1 * | 4/2004 | Molino et al. ................. | 623/26 |
| 2004/0083008 | A1 * | 4/2004 | Molino et al. ................. | 623/44 |

FOREIGN PATENT DOCUMENTS

| | | | |
|---|---|---|---|
| JP | A-11-019105 | | 1/1999 |
| JP | A-2001-218778 | | 8/2001 |
| JP | 2005087347 A | * | 4/2005 |
| JP | A-2005-087347 | | 4/2005 |

* cited by examiner

*Primary Examiner*—David Isabella
*Assistant Examiner*—Jacqueline Woznicki
(74) *Attorney, Agent, or Firm*—Oliff & Berridge, PLC

(57) ABSTRACT

In a prosthetic leg installed with a hydraulic cylinder for adjusting bending and extension resistance of a knee joint portion, a buffer device is provided between a lower leg portion and a foot portion below the knee joint portion for displacing movably in opposite directions when the toe and the heel of the foot portion contact the ground, respectively. An extension passage and a bending passage are provided in the hydraulic cylinder, a toe grounding closing valve is provided in the bending passage, and a heel grounding closing valve is provided in the bending passage. The toe grounding closing valve and the heel grounding closing valve are connected in an interlocking manner by a closing valve connecting/operating member such that valve open/close orientations thereof are set in opposite directions. A grounding detection member is provided for detecting movable displacement of the buffer device and displacing movably when the toe or heel on the foot portion of the prosthetic leg contacts the ground, and a grounding transmission member is provided for transmitting the movable displacement of the grounding detection member to the closing valve connecting/operating member to cause the closing valve connecting/operating member to displace movably.

6 Claims, 10 Drawing Sheets

PROSTHETIC LEG

INCORPORATION BY REFERENCE

The disclosure of Japanese Patent Application No. 2007-063154 filed on Mar. 13, 2007 including the specification, drawings and abstract is incorporated herein by reference in its entirety.

BACKGROUND OF THE INVENTION

1. Field of the Invention

The present invention relates to a prosthetic leg which is attached to a leg that has been amputated proximal to the knee as a substitute leg and has a hydraulic cylinder for adjusting the bending and extension resistance of a knee joint portion, and which enables walking on stairs, slopes, and level ground without buckling of the knee by employing the movable displacement of a buffer device provided between a lower leg portion and a foot portion below the knee joint portion to lock the knee of the prosthetic leg so that the knee does not buckle when the toe of the prosthetic leg contacts the ground and increase the knee bend resistance of the prosthetic leg when the heel of the prosthetic leg contacts the ground so that the knee bends slowly, and more particularly to a prosthetic leg which enables smooth walking on level ground and down slopes and stairs by allowing the knee to bend without locking the knee when a knee bending operation is performed continuously from a state in which the knee is extended while switching from heel grounding to toe grounding during walking.

2. Description of the Related Art

Japanese Patent Application Publication No. JP-A-H11-19105, Japanese Patent Application Publication No. JP-A-2001-218778, and so on, for example, are known as prosthetic legs that are attached to an amputated leg proximal to the knee as a substitute leg and provided with a pneumatic cylinder or a hydraulic cylinder used to adjust the bending/extension resistance of a knee joint portion.

Further, Japanese Patent Application Publication No. JP-A-2005-87347 has been filed as a prosthetic leg which enables walking on stairs, slopes, and level ground without buckling of the knee by controlling bending and extension resistance in the knee of the prosthetic leg, during use, without detecting muscle contraction in the stump portion of the amputated leg, to lock the knee of the prosthetic leg so that the knee does not buckle when the toe of the prosthetic leg contacts the ground and increase the knee bend resistance of the prosthetic leg when the heel of the prosthetic leg contacts the ground so that the knee bends slowly.

In the invention of Japanese Patent Application Publication No. JP-A-2005-87347, walking on stairs, slopes, and level ground without buckling of the knee is made possible by controlling the bending and extension resistance in the knee of the prosthetic leg during use, without detecting muscle contraction in the stump portion of the amputated leg, to lock the knee of the prosthetic leg so that the knee does not buckle when the toe of the prosthetic leg contacts the ground and increase the knee bend resistance of the prosthetic leg when the heel of the prosthetic leg contacts the ground so that the knee bends slowly.

In the invention of Japanese Patent Application Publication No. JP-A-2005-87347, a toe grounding lock valve 76 and a heel grounding lock valve are disposed independently of each other, leading to a corresponding increase in the number of components, an increase in the amount of required space, and a corresponding increase in the structural complexity of the narrow hydraulic cylinder. Moreover, since the two valves are operated independently, a malfunction in which both the toe grounding lock valve and the heel grounding lock valve enter an open state or both valves enter a closed state may occur.

Further, in the invention of Japanese Patent Application Publication No. JP-A-2005-87347, during walking on level ground, the knee is not locked when the toes contact the ground with the knee in an extended state and when the knee bends to a small angle between 20 and 30 degrees, for example, but when the knee bends beyond this point, the knee is locked. Once locked, the knee does not bend further, and therefore it may be impossible to move smoothly forward when the toes contact the ground.

(Section A of FIG. 9)

Furthermore, when the heel of the prosthetic leg contacts the ground while walking down a slope or stairs, the knee bend resistance is increased so that the knee bends slowly, but when heel grounding switches to toe grounding knee bending is locked, preventing smooth walking.

As a preventative measure, locking may be prevented until the knee bends to 40 or 50 degrees, but in so doing, locking is not performed until the knee bends to 40 or 50 degrees even when walking upstairs, and as a result, it becomes difficult to walk upstairs.

SUMMARY OF THE INVENTION

The present invention has been designed to control bending and extension resistance in the knee of a prosthetic leg during use without detecting muscle contraction in the stump portion of the amputated leg, and an object thereof is to provide a prosthetic leg which achieves structural simplification and malfunction prevention by connecting a toe grounding closing valve and a heel grounding closing valve by a closing valve connecting/operating member such that the open/close orientations of the valves are opposite to each other, enables walking on stairs, slopes, and level ground without buckling of the knee by employing the movable displacement of a buffer device provided between a lower leg portion and a foot portion below a knee joint portion to lock the knee of the prosthetic leg so that the knee does not buckle when the toes of the prosthetic leg contact the ground, and increase the knee bend resistance of the prosthetic leg when the heel of the prosthetic leg contacts the ground so that the knee bends slowly, and enables smooth walking on level ground and down slopes and stairs by allowing the knee to bend without locking the knee when a knee bending operation is performed continuously from a state in which the knee is extended while switching from heel grounding to toe grounding during walking.

To achieve this object, an invention according to a first aspect is a prosthetic leg which is attached to a leg that has been amputated proximal to the knee as a substitute leg, and which is installed with a hydraulic cylinder for adjusting bending and extension resistance of a knee joint portion, wherein, when a piston provided in a cylinder chamber of the hydraulic cylinder moves in a direction for extending the prosthetic leg, an extension passage allows passage of a liquid in a first cylinder chamber into a second cylinder chamber, and when the piston provided in the cylinder chamber of the hydraulic cylinder moves in a direction for bending the prosthetic leg, a bending passage allows passage of the liquid in the second cylinder chamber into the first cylinder chamber. The bending passage bifurcates into two at a midway point thereon so as to connect to the first cylinder chamber side, a toe grounding closing valve being provided at a midway point on the bending passage prior to bifurcation for closing the bending passage when a toe on a foot portion of the prosthetic leg contacts the ground, and a heel grounding closing valve being provided at a midway point on one of the bending passages following bifurcation for closing the bending passage when a heel on the foot portion of the prosthetic leg contacts the ground. The toe grounding closing valve and the heel grounding closing valve are connected by a closing valve connecting/operating member for connecting the toe grounding closing valve and the heel grounding closing valve in an interlocking manner such that valve open/close orientations thereof are set in opposite directions.

Further, to achieve the object described above, an invention according to a second aspect is a prosthetic leg which is attached to a leg that has been amputated proximal to the knee as a substitute leg, and which is installed with a hydraulic cylinder for adjusting bending and extension resistance of a knee joint portion, wherein a buffer device is provided between a lower leg portion and a foot portion below the knee joint portion for displacing movably in opposite directions when a toe of the foot portion and a heel of the foot portion contact the ground, respectively. When a piston provided in a cylinder chamber of the hydraulic cylinder moves in a direction for extending the prosthetic leg, an extension passage allows passage of a liquid in a first cylinder chamber into a second cylinder chamber, and when the piston provided in the cylinder chamber of the hydraulic cylinder moves in a direction for bending the prosthetic leg, a bending passage allows passage of the liquid in the second cylinder chamber into the first cylinder chamber. The bending passage bifurcates into two at a midway point thereon so as to connect to the first cylinder chamber side, a toe grounding closing valve being provided at a midway point on the bending passage prior to bifurcation for closing the bending passage when the toe on the foot portion of the prosthetic leg contacts the ground, and a heel grounding closing valve being provided at a midway point on one of the bending passages following bifurcation for closing the bending passage when a heel on the foot portion of the prosthetic leg contacts the ground. The toe grounding closing valve and the heel grounding closing valve are connected by a closing valve connecting/operating member for connecting the toe grounding closing valve and the heel grounding closing valve in an interlocking manner such that valve open/close orientations thereof are set in opposite directions, a grounding detection member is provided for detecting movable displacement of the buffer device when the toe or the heel on the foot portion of the prosthetic leg contacts the ground, and a grounding transmission member is provided for transmitting movable displacement of the grounding detection member to the closing valve connecting/operating member to make the closing valve connecting/operating member movable. The movable displacement of the grounding detection member caused by grounding of the toe on the foot portion of the prosthetic leg is transmitted by the grounding transmission member to operate the toe grounding closing valve connected to the closing valve connecting/operating member in a closing direction and operate the heel grounding closing valve in an opening direction, and the movable displacement of the grounding detection member caused by grounding of the heel on the foot portion of the prosthetic leg is transmitted by the grounding transmission member to operate the heel grounding closing valve connected to the closing valve connecting/operating member in a closing direction and operate the toe grounding closing valve in an opening direction.

In a preferred aspect according to the first and second aspects, a bypass passage may be provided for allowing the passage of the liquid in the second cylinder chamber toward the first cylinder chamber until the piston moves in a direction for bending the prosthetic leg, the knee of which is extended, to a small angle, one end of the bypass passage being openly connected to an intermediate site on an interior side face of the cylinder chamber, and the other end of the bypass passage being connected to the bending passage on a downstream side of the toe grounding closing valve. Further, an auxiliary passage may be provided between the bending passage on an upstream side of the toe grounding closing valve and the bypass passage, and an auxiliary passage open/close valve may be provided for opening the auxiliary passage when an internal pressure of the bypass passage increases beyond a predetermined internal pressure.

As is evident from the above description, according to the prosthetic leg of the first aspect, the toe grounding closing valve and the heel grounding closing valve are connected in an interlocking manner by the closing valve connecting/operating member such that the open/close orientations thereof are opposite to each other, and therefore a malfunction in which the toe grounding closing valve and the heel grounding closing valve are both closed at the same time can be prevented reliably. Furthermore, the toe grounding closing valve and the heel grounding closing valve are connected and operated by the same closing valve connecting/operating member, enabling a reduction in the number of components and structural simplification.

Hence, when the heel on the foot portion of the prosthetic leg contacts the ground, the knee bend resistance can be increased such that the knee bends slowly, and when the toe on the foot portion of the prosthetic leg contacts the ground, the toe grounding closing valve acts to prevent buckling of the knee at the knee joint portion. As a result, walking on stairs, slopes, and level ground can be performed without buckling of the knee.

More specifically, when the heel on the foot portion of the prosthetic leg contacts the ground, the knee bend resistance of the knee joint portion can be increased such that the knee bends slowly, and thereby, when descending stairs, the knee of the prosthetic leg bends slowly without buckling even if body weight is applied temporarily to the prosthetic leg having increased knee bend resistance due to grounding of the heel. Thus, the other, healthy leg can be raised and then lowered into the position of the stair that is immediately below the stair position of the prosthetic leg while body weight is temporarily applied to the prosthetic leg. At this time, the prosthetic leg bends slowly while the raised healthy leg is placed on the lower stair, and therefore, the healthy leg can be moved close to the position of the lower stair and placed thereon easily by an amount corresponding to the bend of the prosthetic leg. Hence, alternate-leg walking can be performed when descending stairs, unlike in the prior art, and therefore stairs can be descended as smoothly as a healthy person.

Further, when the toe on the foot portion of the prosthetic leg contacts the ground, knee bend of the knee joint portion can be locked, and therefore, when ascending stairs, the knee of the prosthetic leg does not buckle even if body weight is temporarily applied to the prosthetic leg following locking due to toe grounding. Hence, the other, healthy leg can be raised and then lifted into the position of the stair that is immediately above the stair position of the prosthetic leg while body weight is temporarily applied to the prosthetic leg. Thus, alternate-leg walking can be performed when ascending stairs, unlike in the prior art, and therefore stairs can be ascended as smoothly as a healthy person.

Furthermore, when the toe on the foot portion of the prosthetic leg contacts the ground, knee buckling of the knee joint portion is locked, and therefore a standing operation can be performed with the knees of both the prosthetic leg and the healthy leg slightly bent.

According to the prosthetic leg of the second aspect, in addition to the effects of the first aspect, the grounding detection member is provided for detecting movable displacement of the buffer device due to grounding of the toe or heel on the foot portion of the prosthetic leg, and the grounding transmission member is provided for transmitting movable displacement of the grounding detection member to the closing valve connecting/operating member to make the closing valve connecting/operating member movable. Thus, using the movable displacement of the buffer device provided between the lower leg portion and foot portion below the knee joint portion, movable displacement of the grounding detection member caused by grounding of the toe on the foot portion of the prosthetic leg can be transmitted by the grounding transmission member to operate the toe grounding closing valve, which is connected to the closing valve connecting/operating member, in a closing direction and operate the heel grounding closing valve in an opening direction, while movable displacement of the grounding detection member caused by grounding of the heel on the foot portion of the prosthetic leg can be transmitted by the grounding transmission member to operate the heel grounding closing valve, which is connected to the closing valve connecting/operating member, in a closing direction and operate the toe grounding closing valve in an opening direction.

According to a third aspect, when the bypass passage is provided, due to the actions of the bypass passage, knee bending is not locked up to a small angle of 20 to 30 degrees, for example, even when the toe contacts the ground during walking on level ground, and therefore walking on level ground can be performed smoothly.

According to a fourth aspect, when the auxiliary passage is provided on the bypass passage and the toe contacts the ground during walking on level ground such that the knee bends continuously from a state in which the knee is extended, due to the actions of the auxiliary passage open/close valve and the auxiliary passage, bending continues without locking even if the knee bending angle exceeds the small angle of 20 to 30 degrees, for example, and therefore walking on level ground can be performed smoothly.

DETAILED DESCRIPTION OF THE PREFERRED EMBODIMENT

Figure 1:
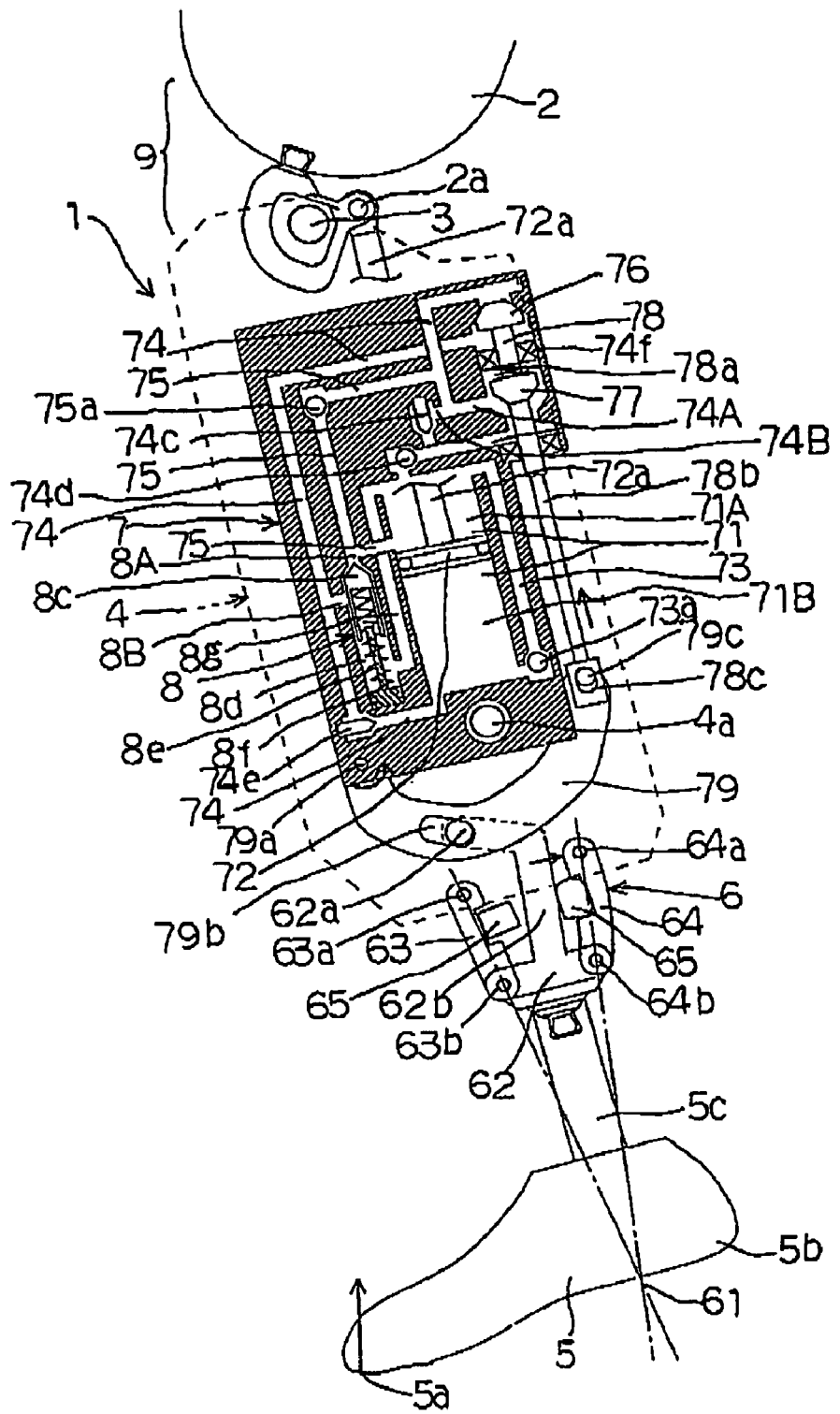
FIG. 1 is a side sectional view showing the main parts of a prosthetic leg during toe grounding according to an embodiment of the present invention.

The present invention will now be described in specific detail on the basis of embodiment illustrated in the drawings.

Figure 2:
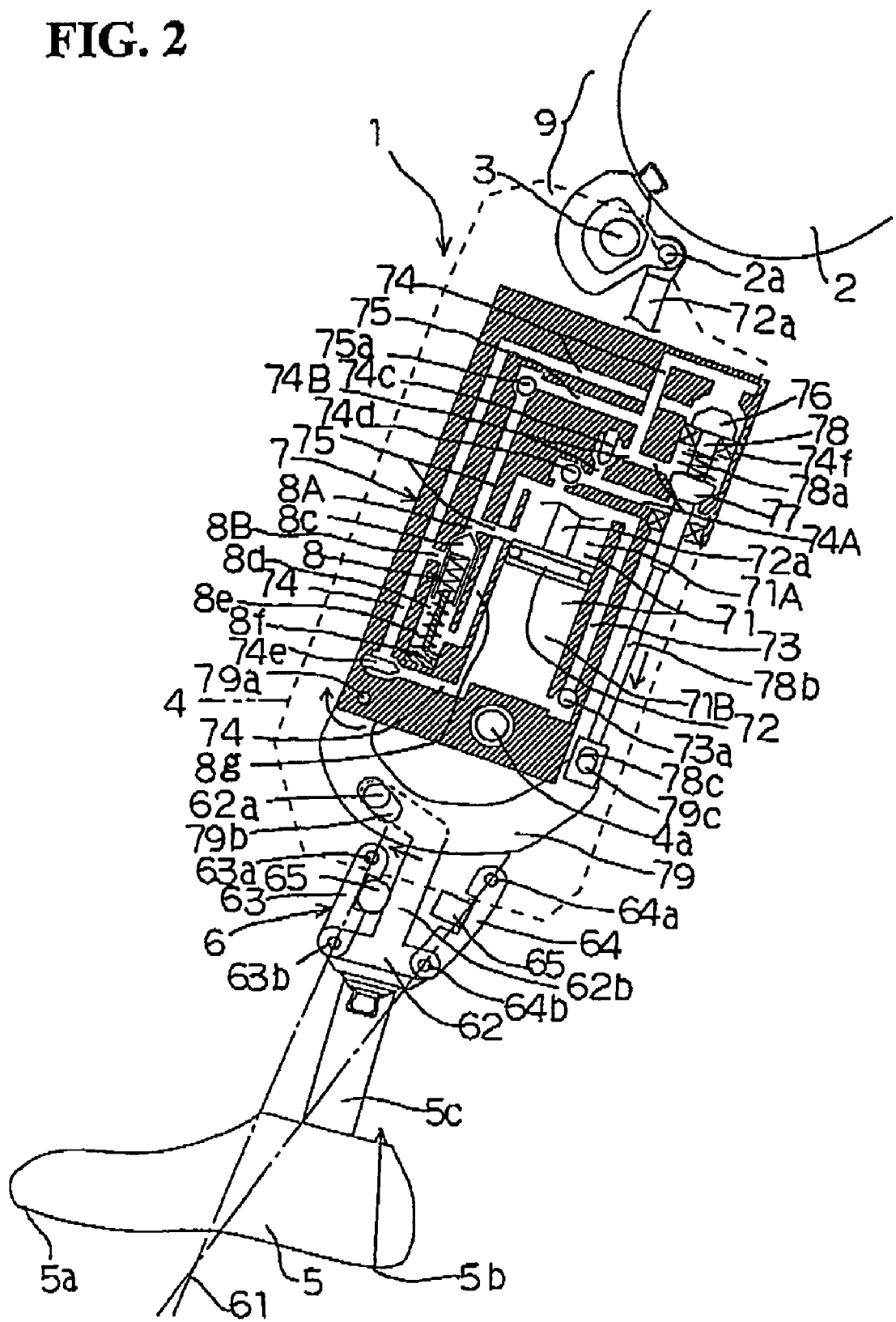
FIG. 2 is a side sectional view showing the main parts of the prosthetic leg during heel grounding according to an embodiment of the present invention.
Figure 3:
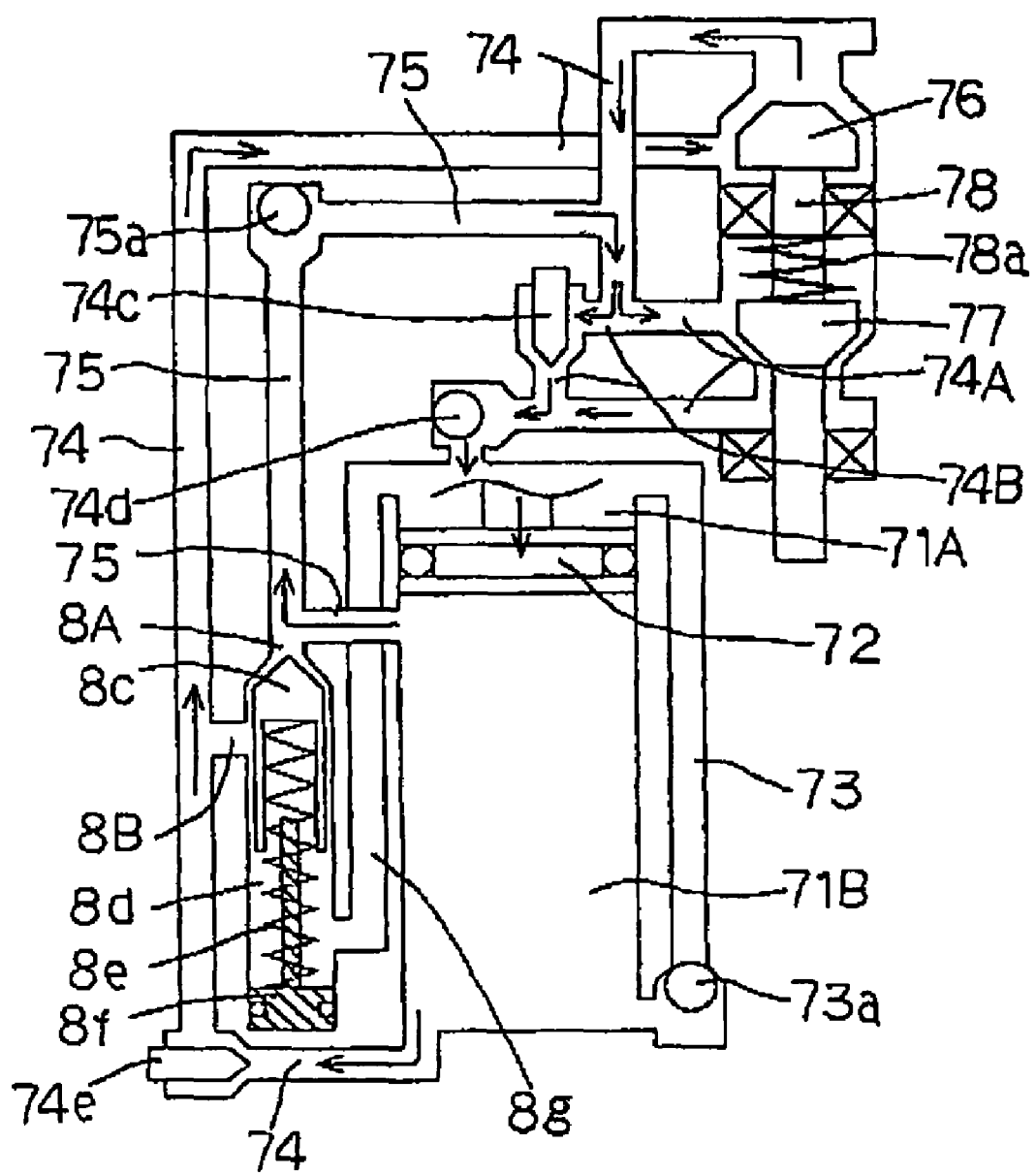
FIG. 3 is a circuit diagram of a hydraulic cylinder when a knee bends slightly from an extended state while a toe grounding closing valve is open when a toe does not contact the ground, according to an embodiment of the present invention.
Figure 4:
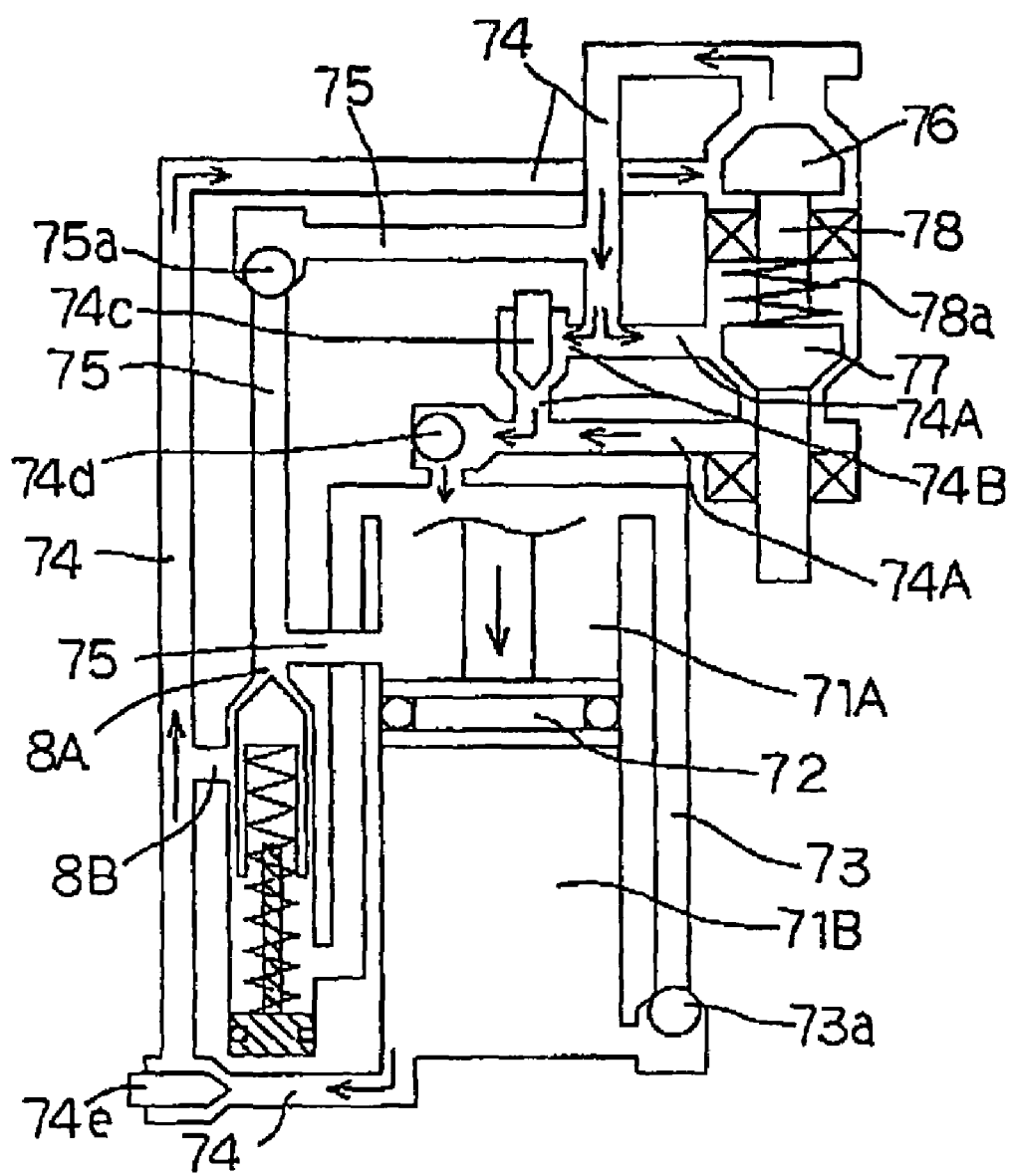
FIG. 4 is a circuit diagram of the hydraulic cylinder when the knee bends to or above a small angle of 20 to 30 degrees, for example, while the toe grounding closing valve is open when a toe does not contact the ground, according to an embodiment of the present invention.
Figure 5:
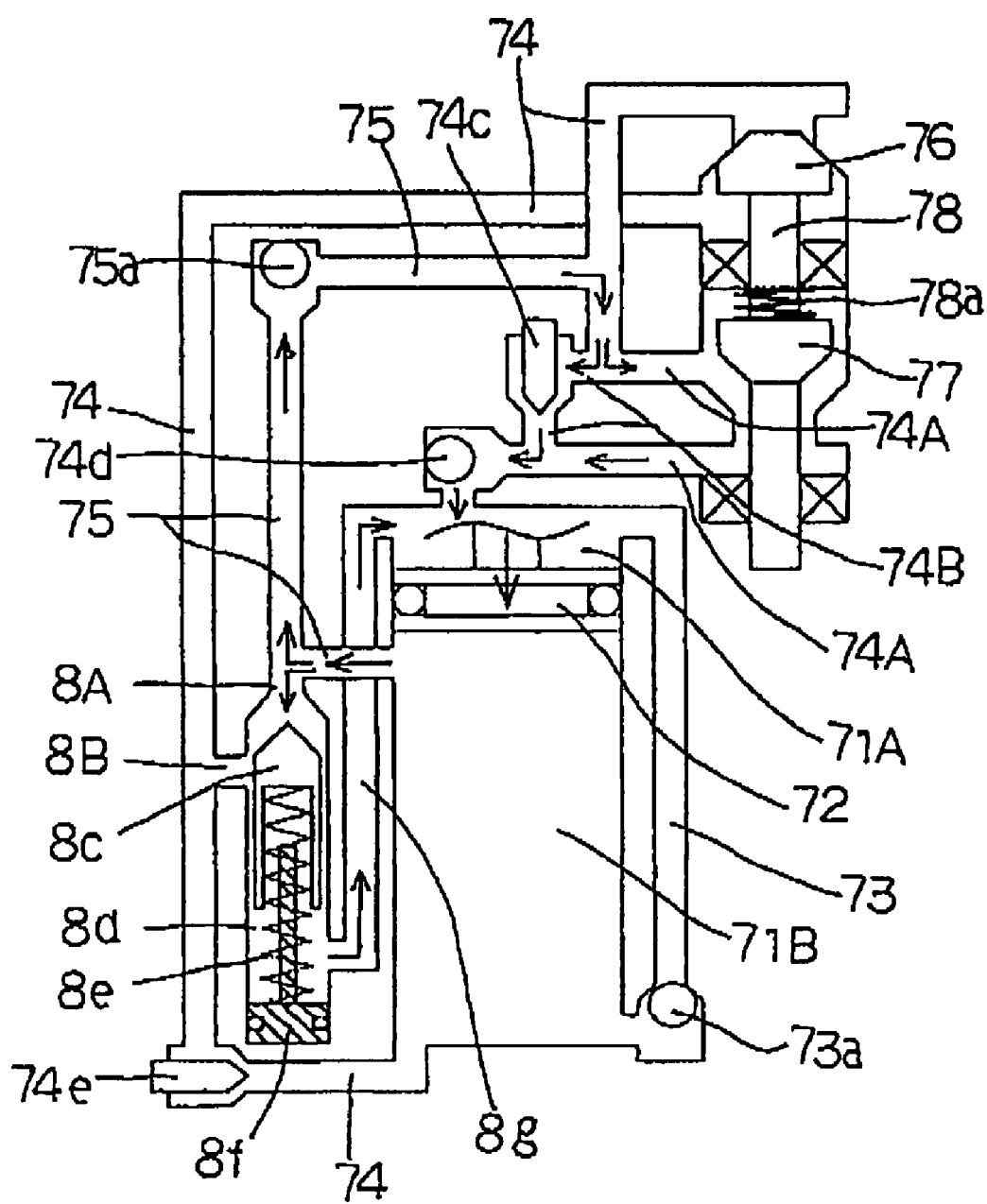
FIG. 5 is a circuit diagram of the hydraulic cylinder when the knee bends slightly from an extended state while the toe grounding closing valve is closed during toe grounding, according to an embodiment of the present invention.
Figure 6:
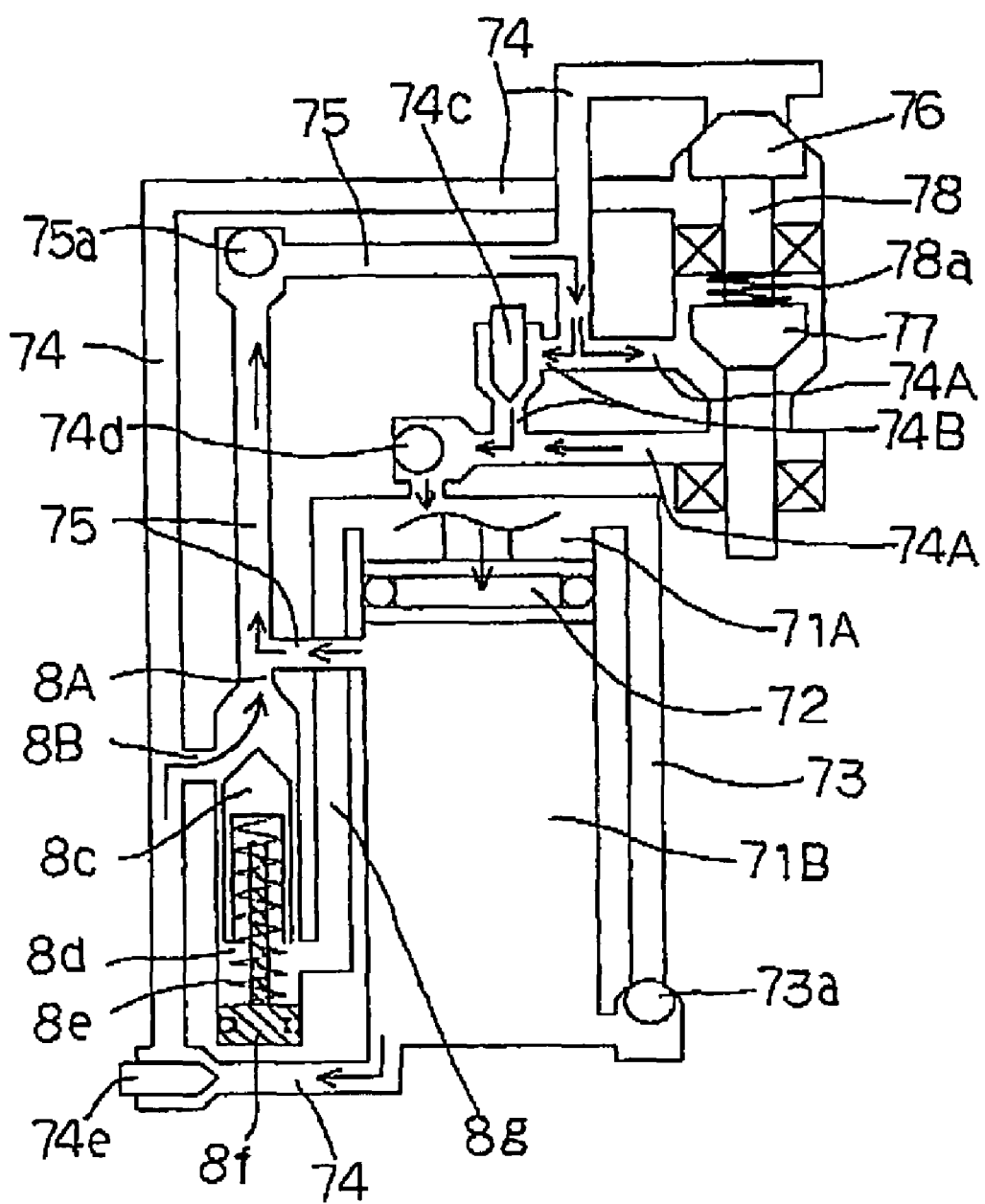
FIG. 6 is a circuit diagram of the hydraulic cylinder when the knee bends slightly from an extended state while the toe grounding closing valve is closed and an auxiliary passage is open during toe grounding, according to an embodiment of the present invention.
Figure 7:
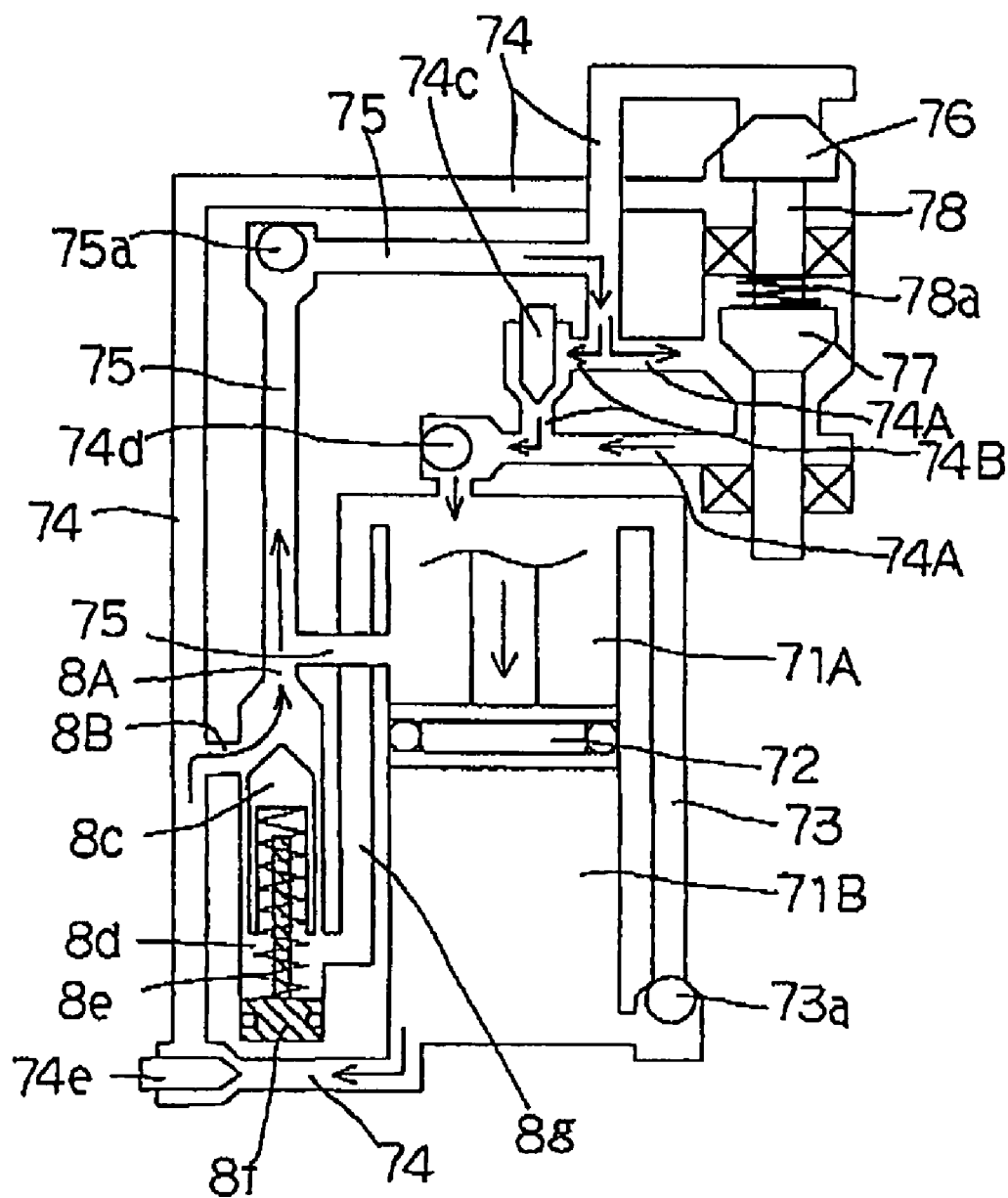
FIG. 7 is a circuit diagram of the hydraulic cylinder when the knee bends to or above a small angle of 20 or 30 degrees, for example, while the toe grounding closing valve is closed and the auxiliary passage is open during toe grounding, according to an embodiment of the present invention.
Figure 8:
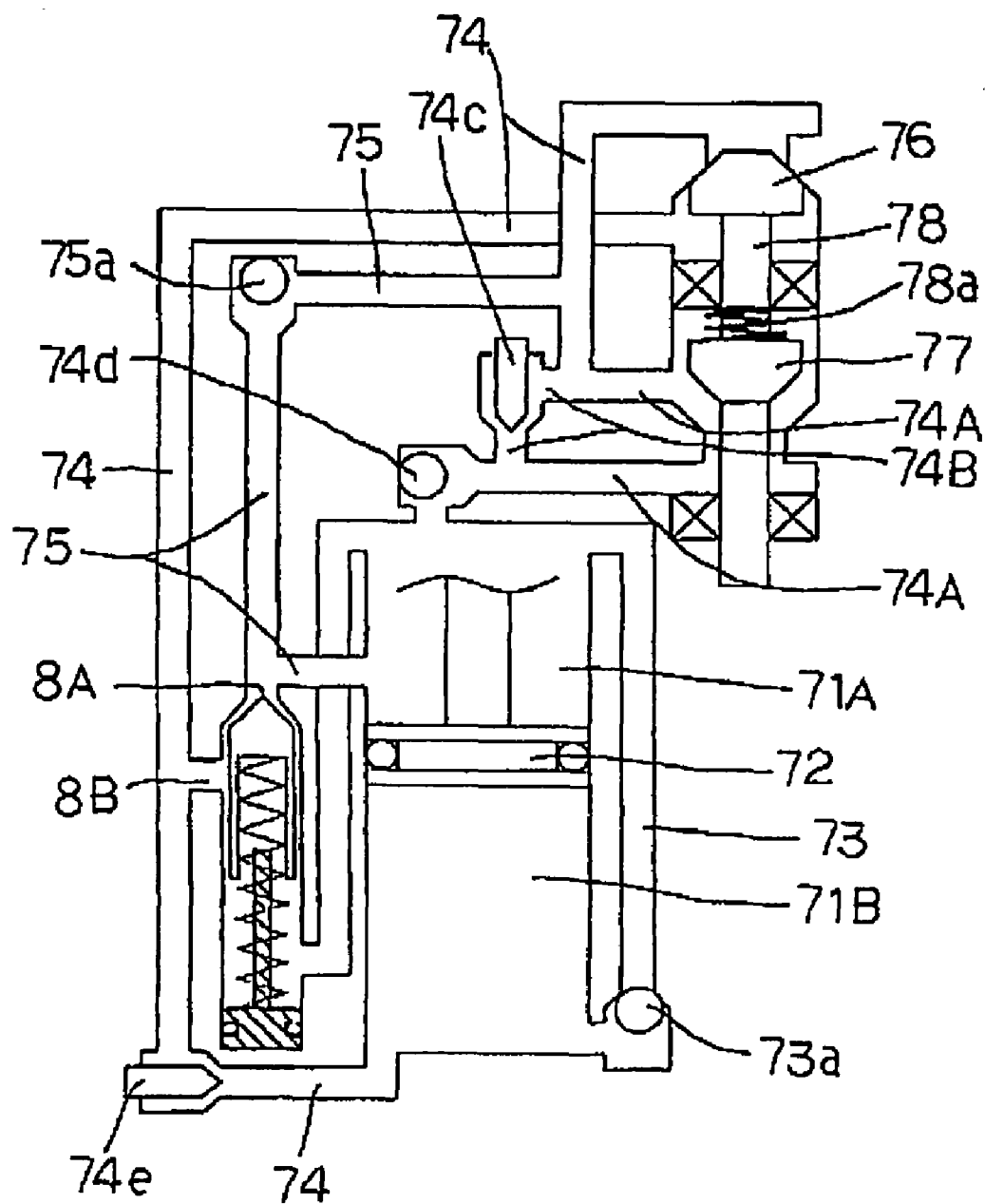
FIG. 8 is a circuit diagram of the hydraulic cylinder when a bending operation is halted after the knee has bent to or above a small angle of 20 to 30 degrees, for example, such that the auxiliary passage closes while the toe grounding closing valve is closed during toe grounding, according to an embodiment of the present invention.
Figure 9:
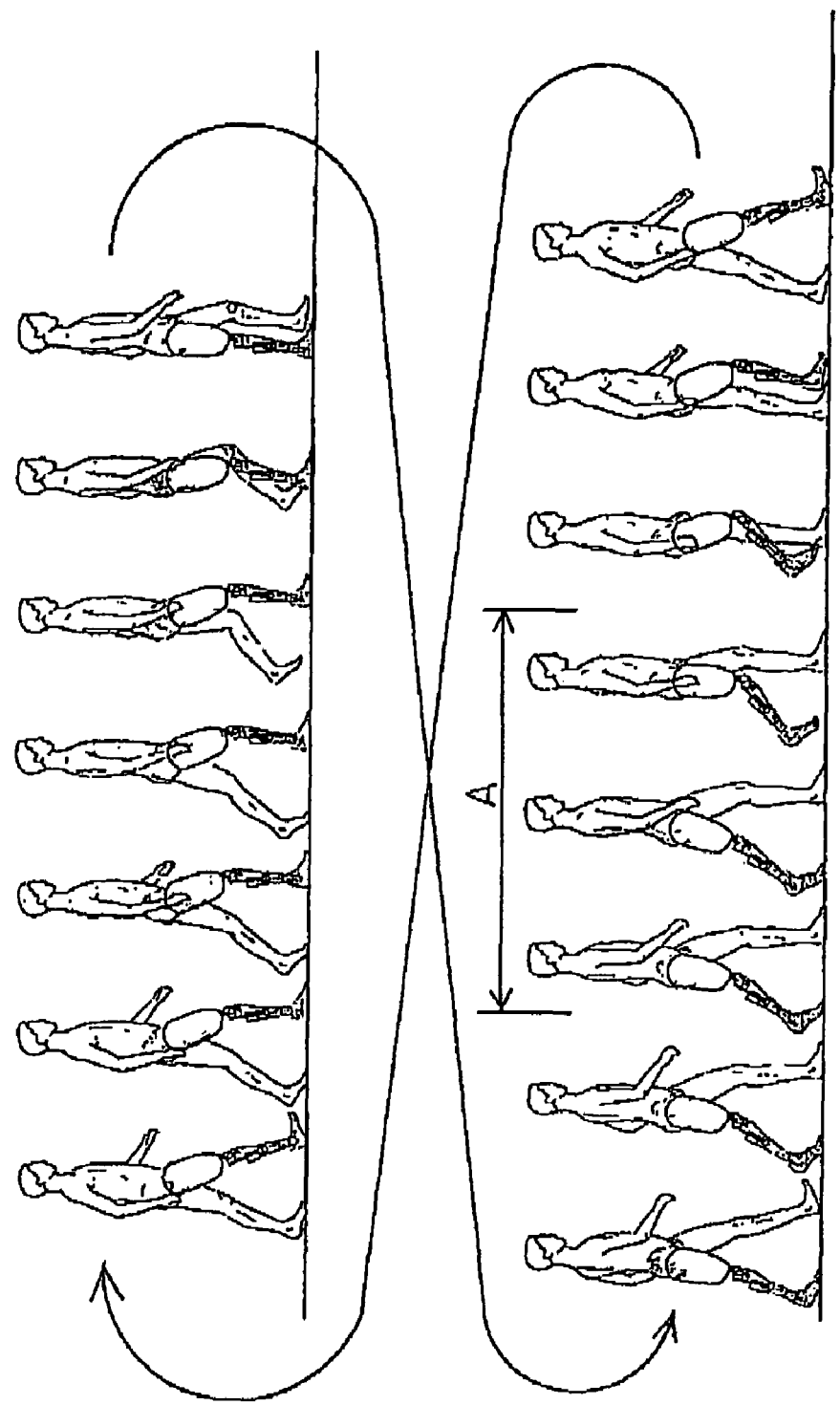
FIG. 9 is a continuous analysis diagram of level ground walking.

Here, FIG. 1 is a side sectional view showing the main parts of a prosthetic leg during toe grounding, FIG. 2 is a side sectional view showing the main parts of the prosthetic leg during heel grounding and FIGS. 3 to 8 are circuit diagrams of a hydraulic cylinder.

In FIGS. 1 and 2, a prosthetic leg 1 is mainly constituted by a thigh socket 2 which is attached to a stump portion of an amputated leg, a lower leg portion 4 which is connected to the bottom of the thigh socket 2 by a knee shaft 3 so as to be capable of moving in a front-rear direction, a foot portion 5 below the lower leg portion 4, a buffer device 6 provided between the lower leg portion 4 and the foot portion 5, a hydraulic cylinder 7 for applying bending and extension resistance to the knee shaft 3, and so on. Using a knee joint portion 9 constituted by the knee shaft 3 and the hydraulic cylinder 7, bending and extension can be performed in a similar manner to the knee of a healthy human leg.

The thigh socket 2 has a cavity part on an upper half portion side thereof, and an upper end of the thigh socket 2, which serves as the upper end side of the cavity part, is open so that the stump portion of the amputated leg can be inserted into and attached to the interior cavity part through the open part in the upper end thereof.

The buffer device 6 exhibits a cushioning function between the thigh socket 2 and knee shaft 3 and the lower leg portion 4 and foot portion 5, and also functions as a sensor for sensing the grounding of a toe 5a on the foot portion 5 of the lower leg portion 4 and a heel 5b of the foot portion 5 through movable displacement generated thereby in opposite directions through a reactive force from the ground surface when the toe 5a contacts the ground and a reactive force from the ground surface when the heel 5b contacts the ground, respectively.

The buffer device 6 functions to rotate the lower leg portion 4 and the foot portion S relatively about a horizontal axis centering on a virtual rotary center 61 of a link structure by generating movable displacement in opposite directions when the toe 5a and the heel 5b of the foot portion 5 respectively contact the ground. The buffer device 6 is constituted by a central base plate 62 connected with play remaining to a grounding detection member 79 to be described below, which is connected to a lower end side of the hydraulic cylinder 7 attached to the lower leg portion 4 so as to be free to rotate vertically via an elongated hole 79b to be described below, and a front portion link plate 63 and a rear portion link plate 64 provided at the front and rear of the central base plate 62 to form the link structure.

The central base plate 62 is formed such that an upper portion side thereof in the drawing is oriented in the direction of the elongated hole 79b of the grounding detection member 79 to be described below, or in other words so as to incline diagonally upward toward the toe 5a side in the drawing. A connecting shaft 62a engaged with the elongated hole 79b of the grounding detection member 79 to be described below is attached to a side face of the central base plate 62 on the tip end side of the diagonally upward incline. The connecting shaft 62a moves slightly freely within the elongated hole 79b, thereby coming into contact with the two interior end sides of the elongated hole 79b such that the grounding detection member 79 to be described below is rotated vertically about a pivot shaft 79a to be described below and thus movably displaced. Further, a lower portion side of the central base plate 62 in the drawing is enlarged to the front and rear, and a foot connecting rod 5c connected to the foot portion 5 is attached in a downward orientation to the lower surface side thereof.

An upper portion of the front portion link plate 63 is rotatably connected to a lower end side front portion of the lower leg portion 4 by an upper portion link shaft 63a, and a lower portion of the front portion link plate 63 is rotatably connected to a lower portion side front portion of the central base plate 62 by a lower portion link shaft 63b. Further, an upper portion of the rear portion link plate 64 is rotatably connected to a lower end side rear portion of the lower leg portion 4 by an upper portion link shaft 64a, and a lower portion of the rear portion link plate 64 is rotatably connected to a lower portion side rear portion of the central base plate 62 by a lower portion link shaft 64b.

The virtual rotary center 61 of the buffer device 6 is positioned at the intersection point of a straight extension line joining the upper portion link shaft 63a and lower portion link shaft 63b of the front portion link plate 63 and a straight extension line joining the upper portion link shaft 64a and lower portion link shaft 64b of the rear portion link plate 64. As regards the link structure, even when the virtual rotary center 61 is set near the front portion side of the foot portion 5, the link structure does not jut out onto the front portion side. The link structure is provided such that the virtual rotary center 61 of the buffer device 6 is positioned between the toe 5a and the heel 5b of the foot portion 5 of the prosthetic leg 1.

The central base plate 62, to the front and rear lower portion sides of which the lower portion link shaft 63b of the front portion link plate 63 and the lower portion link shaft 64b of the rear portion link plate 64 are connected, extends upward from a central portion thereof When the toe 5a of the foot portion 5 contacts the ground in the example shown in FIG. 1, an intermediate portion side 62b of the central base plate 62 is moved relatively to the rear portion link plate 64 side by a clockwise rotary moment produced by a reactive force acting on the toe 5a from the ground surface, and conversely, when the heel 5b of the foot portion 5 contacts the ground in the example shown in FIG. 2, the intermediate portion side 62b of the central base plate 62 is moved relatively to the front portion link plate 63 side by a counter-clockwise rotary moment produced by a reactive force acting on the heel 5b from the ground surface.

Elastic bodies 65 exhibiting a cushioning function, or in other words a buffering function, are provided respectively between the front portion link plate 63 and the intermediate portion side 62b of the central base plate 62 and between the intermediate portion side 62b and the rear portion link plate 64. The elastic bodies are made from rubber, for example. The front portion link plate 63 and rear portion link plate 64 provided with the elastic bodies 65 are indented in recessed form on a rear surface side of the former and a front surface side of the latter so that the elastic bodies 65 can be sandwiched easily between the respective link plates 63, 64 and the intermediate portion side 62b.

The hydraulic cylinder 7 adjusts the bending and extension resistance of the knee shaft 3, and is installed in the interior of the lower leg portion 4 beneath the knee shaft 3. A cylinder chamber 71 is provided in the interior of the hydraulic cylinder 7, and a piston 72 is installed slidably within the cylinder chamber 71.

One end of a piston rod 72a is fixed to the piston 72, and the other end side of the piston rod 72a extends to the exterior of the hydraulic cylinder 7. In this embodiment, the hydraulic cylinder 7 is attached in a vertical orientation such that the piston rod 72a extends upward and the upper end of the piston rod 72a, i.e. the other end thereof, is connected rotatably to a rod shaft 2a attached slightly toward the rear side of a rotary center portion of the knee shaft 3 in a left-right width direction of the prosthetic leg 1.

Further, a lower end side of the hydraulic cylinder 7, which is attached in a vertical direction to the interior of the lower leg portion 4, is connected rotatably to a cylinder shaft 4a attached to a lower portion side of the interior of the lower leg portion 4 in the left-right width direction of the prosthetic leg 1.

The interior of the cylinder chamber 71 in the hydraulic cylinder 7 is divided into two chambers on either side of the piston 72. More specifically, in FIGS. 1 and 2, the cylinder chamber 71 is divided into a first cylinder chamber 71A on the upper side of the piston 72 and a second cylinder chamber 71B on the lower side of the piston 72, The piston rod 72a penetrates the interior of the first cylinder chamber 71A.

A liquid such as oil, for example, is sealed into the interior of the cylinder chamber 71 divided into two chambers on either side of the piston 72. An extension passage 73, a bending passage 74, and a bypass passage 75 are provided in the hydraulic cylinder 7 such that the liquid in the two chambers on either side of the piston 72 flows in an opposite direction to the movement direction of the piston 72 as the piston 72 moves. If necessary, an auxiliary passage 8 is also provided in the hydraulic cylinder 7.

The extension passage 73 is a passage through which the interior liquid passes when the piston 72 moves in a direction for extending the prosthetic leg 1, and the two ends of the extension passage 73 are openly connected to the two interior end sides of the cylinder chamber 71. More specifically, one end of the extension passage 73 is openly connected to the end portion side of the first cylinder chamber 71A, and the other end of the extension passage 73 is openly connected to the end portion side of the second cylinder chamber 71B.

The extension passage 73 is provided with a check valve 73a that allows the liquid in the first cylinder chamber 71A to move into the second cylinder chamber 71B and prevents the liquid from moving in the opposite direction. The check valve 73a functions to allow movement of the liquid from the first cylinder chamber 71A to the second cylinder chamber 71B and prevent opposite movement, i.e. movement of the liquid from the second cylinder chamber 71B to the first cylinder chamber 71A.

The bending passage 74 is a passage through which the interior liquid passes when the piston 72 moves in a direction for bending the prosthetic leg 1, and the two ends of the bending passage 74 are openly connected to the two interior end sides of the cylinder chamber 71. More specifically, one end of the bending passage 74 is openly connected to the end portion side of the second cylinder chamber 71B, and the other end of the bending passage 74 is openly connected to the end portion side of the first cylinder chamber 71A.

Note that the bending passage 74 bifurcates into two passages, namely a bending passage 74A and a bending passage 74B, at the location of a toe grounding closing valve 76 to be described below. The two passages then re-converge and are openly connected to the end portion side of the first cylinder chamber 71A.

The toe grounding closing valve 76 is provided at a midway point in the bending passage 74 from the second cylinder chamber 71B to the first cylinder chamber 71A. A heel grounding closing valve 77 is provided at a midway point in the bifurcated bending passage 74A, and a flow control valve 74c is provided at a midway point in the bifurcated bending passage 74 B.

The flow control valve 74c is a valve for adjusting the flow rate of the liquid flowing through one of the two bifurcated bending passages 74B by adjusting the surface area of the passage cross-section of the bending passage 74B at the location of the toe grounding closing valve 76. A needle valve, for example, is used as the flow control valve 74c. When the heel 5b of the foot portion 5 contacts the ground, the flow control valve 74c increases the bend resistance of the knee shaft 3 by reducing the flow rate of the flowing liquid so that the knee of the prosthetic leg 1 bends slowly.

A check valve 74d for allowing the liquid in the second cylinder chamber 71B to move into the first cylinder chamber 71A and preventing movement of the liquid in the opposite direction is provided in the bending passage 74 on the downstream side of the heel grounding closing valve 77 and the flow control valve 74c. The check valve 74d is provided in the re-converged bending passage 74 on the downstream side of the flow control valve 74c and heel grounding closing valve 77 after the bending passage 74 bifurcates into the bending passage 74A and the bending passage 74B.

A flow control valve 74e is also provided in the bending passage 74 on the upstream side of the location of an open connection to an auxiliary passage 8B to be described below. The flow control valve 74e is a valve for adjusting the flow rate of the liquid flowing through the bending passage 74 by adjusting the surface area of the passage cross-section of the bending passage 74 on the upstream side of the location of the open connection to the auxiliary passage 8B to be described below. A needle valve, for example, is used as the flow control valve 74e. The flow control valve 74e increases the bend resistance of the knee shaft 3 by reducing the flow rate of the flowing liquid so that the knee of the prosthetic leg 1 bends slowly.

When the toe 5a of the foot portion 5 of the prosthetic leg 1 contacts the ground such that the upper end side of the intermediate portion side 62b of the central base plate 62 in the buffer device 6 is moved relatively in the clockwise direction of FIG. 1, or in other words to the rear portion link plate 64 side, by the reactive force from the ground surface, the toe grounding closing valve 76 is operated by an action of the grounding detection member 79, which displaces movably having sensed this movement, to close the bending passage 74 such that the liquid is prevented from moving from the second cylinder chamber 71B to the first cylinder chamber 71A.

When the liquid is prevented from moving from the second cylinder chamber 71B to the first cylinder chamber 71A by the action of the toe grounding closing valve 76, movement of the piston 72 in a direction for bending the prosthetic leg 1, or in other words movement to the second cylinder chamber 71B side on the lower side of FIG. 1, is prevented.

When the heel 5b of the foot portion 5 of the prosthetic leg 1 contacts the ground such that the upper end side of the intermediate portion side 62b of the central base plate 62 in the buffer device 6 is moved relatively in the counter-clockwise direction of FIG ; 2, or in other words to the front portion link plate 63 side, by the reactive force from the ground surface, the heel grounding closing valve 77 is operated by the action of the grounding detection member 79, which displaces movably having sensed this movement, to close the bending passage 74A such that the liquid is prevented from flowing through the bending passage 74A to move from the second cylinder chamber 71B to the first cylinder chamber 71A.

Due to the action of the heel grounding closing valve 77, the liquid is prevented from flowing through the bending passage 74A to move from the second cylinder chamber 71B to the first cylinder chamber 71A. Hence, the liquid enters the first cylinder chamber 71A through the flow control valve 74c of the bending passage 74B, but since the flow rate thereof is restricted by the flow control valve 74c, movement of the piston 72 slows and the resistance applied to the piston 72 when moving in a direction for bending the prosthetic leg 1, or in other words the resistance when moving to the second cylinder chamber 71B side on the lower side of FIG : 2, increases. As a result, the piston 72 moves slowly.

The toe grounding closing valve 76 and the heel grounding closing valve 77 are connected to an identical closing valve connecting/operating member 78. The closing valve connecting/operating member 78 connects the toe grounding closing valve 76 and the heel grounding closing valve 77 in an interlocking manner such that the open/close orientations of the two valves are opposite to each other, or in other words such that when one closing valve is open, the other is closed. More specifically, the closing valve connecting/operating member 78 connects the toe grounding closing valve 76 and the heel grounding closing valve 77 in an interlocking manner so as to close the heel grounding closing valve 77 when the toe grounding closing valve 76 is open, and open the heel grounding closing valve 77 when the toe grounding closing valve 76 is closed.

In the drawing, the closing valve connecting/operating member 78 is constituted by a rod-form body, for example. Further, the rod-form closing valve connecting/operating member 78 is disposed substantially vertically such that the toe grounding closing valve 76 is connected to the upper portion of the closing valve connecting/operating member 78 and the heel grounding closing valve 77 is connected to the lower portion of the closing valve connecting/operating member 78. The closing valve connecting/operating member 78 moves in a substantially vertical direction so as to penetrate a partition 74f that separates the pre-bifurcation bending passage 74, in which the toe grounding closing valve 76 on the upper side of the drawing is disposed, from the post-bifurcation bending passage 74A in which the heel grounding closing valve 77 on the lower side of the drawing is disposed.

A return spring 78a constituted by a coil spring, for example, is attached to the closing valve connecting/operating member 78 that moves in a substantially vertical direction in the drawing to return the closing valve connecting/operating member 78 to a neutral position after the closing valve connecting/operating member 78 has moved upward and an upward force acting thereon has been released. In the drawing, the return spring 78a is mounted between the partition 74f on the lower side of the toe grounding closing valve 76 and the heel grounding closing valve 77.

Further, when the closing valve connecting/operating member 78 moves upward in the drawing, the toe grounding closing valve 76 thereabove is moved in a closing direction so as to close, while the heel grounding closing valve 77 therebelow is moved in an opening direction so as to open. Conversely, when the closing valve connecting/operating member 78 moves downward in the drawing, the toe grounding closing valve 76 thereabove is moved in an opening direction so as to open, while the heel grounding closing valve 77 therebelow is moved in a closing direction so as to close.

The toe grounding closing valve 76 and the heel grounding closing valve 77 are connected in an interlocking manner by the closing valve connecting/operating member 78 such that the open/close orientations thereof are opposite to each other, and therefore a malfunction in which the toe grounding closing valve 76 and the heel grounding closing valve 77 both enter a closed state, for example, can be avoided reliably. Further, the toe grounding closing valve 76 and the heel grounding closing valve 77 are operated by the same closing valve connecting/operating member 78, enabling a corresponding reduction in the number of components and structural simplification.

The grounding detection member 79, which displaces movably upon detection of movable displacement of the buffer device 6 when the toe and heel of the foot portion 5 of the prosthetic leg 1 contact the ground, is also provided. The grounding detection member 79 is provided vertically between the hydraulic cylinder 7 and the buffer device 6. The grounding detection member 79 is formed in a substantially semicircular arc shape bent into a convex form that faces downward in the drawing, for example. One end side of the grounding detection member 79 bent into a downwardly facing convex shape, in the drawing the left end side near the toe 5a of the foot portion 5, is supported by a pivot shaft 79a so as to be free to rotate vertically about an end portion of the lower end side of the hydraulic cylinder 7 near the toe 5a.

The elongated hole 79b having an elliptical shape, for example, is formed so as to incline diagonally slightly downward toward the heel 5b side in a location slightly nearer the toe 5a of the foot portion 5 than the center of the grounding detection member 79 bent into a downwardly facing convex shape in the drawing. A connecting shaft 62a attached to a side face on the diagonally upward-inclined tip end side of the aforesaid central base plate 62 is engaged with the interior of the elongated hole 79b with play remaining, or in other words so as to be capable of slight free movement, and when the connecting shaft 62a contacts either one of the two interior ends of the elongated hole 79b, the grounding detection member 79 rotates vertically about the pivot shaft 79a so as to be movably displaced.

A grounding transmission member 78b for causing the closing valve connecting/operating member 78 to displace movably in the vertical direction by transmitting the movable displacement of the grounding detection member 79 to the closing valve connecting/operating member 78 is connected in an interlocking manner to the other end side of the grounding detection member 79, in the drawing the right end side near the heel 5b of the foot portion 5, with upward play remaining, or in other words so as to be capable of slight free vertical movement.

A rod-form body, for example, is used as the grounding transmission member 78b. In the drawing, the upper portion side of the grounding transmission member 78b is connected integrally to a lower portion of the closing valve connecting/operating member 78 such that when the grounding transmission member 78b moves vertically, the closing valve connecting/operating member 78 thereabove moves vertically therewith.

Further, a connecting plate is attached to the lower end of the grounding transmission member 78b, and this connecting plate is formed with an elongated hole 78c having an elliptical shape, for example, in an axial center direction of the grounding transmission member 78b. The connecting shaft 79c attached to the right end side face of the grounding detection member 79 is engaged with the interior of the elongated hole 78c. When the connecting shaft 79c moves to one of the two end sides of the elongated hole 78c, the grounding transmission member 78b is moved vertically, whereby the closing valve connecting/operating member 78 connected integrally to the upper portion of the grounding transmission member 78b moves in a substantially vertical direction. As a result, the toe grounding closing valve 76 and the heel grounding closing valve 77 are opened and closed.

In the drawing, the interior of the elongated bole 78c on the lower end side of the grounding transmission member 78b is filled with a buffer material such that when the connecting shaft 79c moves to one of the two end sides of the elongated hole 78c, sudden vertical direction force acting on the grounding transmission member 78b is alleviated by the buffer material, thereby absorbing the shock.

When the toe 5a of the foot portion 5 on the prosthetic leg 1 contacts the ground such that the intermediate portion side 62b of the central base plate 62 of the buffer device 6 moves relatively toward the rear portion link plate 64 side due to the reactive force from the ground surface, the grounding detection member 79 senses this movement and rotates in the counter-clockwise direction of FIG. 1 about the pivot shaft 79a thereby pushing the grounding transmission member 78b upward. As a result, the closing valve connecting/operating member 78 moves upward, thereby closing the toe grounding closing valve 76 such that the bending passage 74 is locked.

As regards the heel grounding closing valve 77, when the heel 5b of the foot portion 5 on the prosthetic leg 1 contacts the ground such that the intermediate portion side 62b of the central base plate 62 of the buffer device 6 moves relatively toward the front portion link plate 63 due to the reactive force from the ground surface, the grounding detection member 79 senses this movement and rotates in the clockwise direction of FIG. 2 about the pivot shaft 79a, thereby pulling the grounding transmission member 78b downward. As a result, the closing valve connecting/operating member 78 moves downward, thereby closing the bending passage 74A and halting the flow of the liquid through the bending passage 74A from the second cylinder chamber 71B to the first cylinder chamber 71A.

The bypass passage 75 allows the interior liquid to flow without being locked until the piston 72 moves in a direction for bending the knee-extended prosthetic leg 1 to a small angle of approximately 20 to 30 degrees, for example, and when the extended prosthetic leg 1 is bent continuously even after the toe 5a of the foot portion 5 contacts the ground while walking on level ground or descending stairs, such that the bending angle exceeds a small angle of 20 to 30 degrees, for example, the bypass passage 75 allows the liquid in the second cylinder chamber 71B to flow toward the first cylinder chamber 71A. In the bypass passage 75, when a bending operation stops once the knee has bent to or above a small angle of 20 to 30 degrees, for example, locking is performed so that the knee cannot bend any further.

While walking on level ground, in order to move forward after the toe 5a on the foot portion 5 of the knee-extended prosthetic leg 1 has contacted the ground, the toe Sa performs an action to kick the ground surface back, and during this process, the knee of the extended prosthetic leg 1 begins to bend. During smooth walking, the knee joint portion 9 bends to or above a small angle of 20 to 30 degrees, for example, but in this case, if a structure that allows unconditional bending up to 40 or 50 degrees is provided, locking is not performed until the knee bends to 40 or 50 degrees when walking upstairs, and this makes walking upstairs difficult.

Hence, the bypass passage 75 allows the knee to bend to or above a small angle of 20 to 30 degrees, for example, when the knee is bent continuously even after the toe 5a on the foot portion 5 of the knee-extended prosthetic leg 1 contacts the ground during smooth walking on level ground. On the other hand, if locking is performed when the knee bends to a small angle of 20 to 30 degrees, for example, after the toe 5a has contacted the ground while walking on level ground, it may be difficult to walk smoothly on level ground when the toe 5a contacts the ground.

One end of the bypass passage 75 is connected openly to an intermediate site on the interior side face of the cylinder chamber 71, and the other end of the bypass passage 75 communicates connectedly with the pre-bifurcation bending passage 74 on the downstream side of the toe grounding closing valve 76. Further, the bypass passage 75 may include the auxiliary passage 8, one end of which is connected to a midway point on the bypass passage 75 and the other end of which is connected to a part of the bending passage 74 on the upstream side of the toe grounding closing valve 76 as necessary.

The intermediate site position on the interior side face of the cylinder chamber 71, to which one end of the bypass passage 75 is openly connected, serves as a location reached by a sealing surface of the piston 72 when the piston 72 moves to the second cylinder chamber 71B side after the knee-extended prosthetic leg 1 has bent to a small angle of approximately 20 to 30 degrees, for example.

The bypass passage 75 allows the liquid to pass through its interior until the piston 72 moves in a direction for bending the knee-extended prosthetic leg 1 to a small angle of approximately 20 to 30 degrees, for example, even in a locked state where the toe grounding closing valve 76 operates to close the bending passage 74. In other words, the liquid in the second cylinder chamber 71B is capable of flowing through the bypass passage 75 and moving from the bending passage 74 on the downstream side of the toe grounding closing valve 76 into the first cylinder chamber 71A through the bending passage 74B and the bending passage 74A on either side of the flow control valve 74c.

A check valve 75a for allowing the liquid to move from the second cylinder chamber 71B to the first cylinder chamber 71A and preventing movement of the liquid from the first cylinder chamber 71A to the second cylinder chamber 71B is provided in the bypass passage 75.

The auxiliary passage 8 constituting a part of the bypass passage 75 functions to allow the knee to bend to or above a small angle of 20 to 30 degrees, for example, when the knee is bent continuously even after the toe 5a of the foot portion 5 has contacted the ground. The auxiliary passage 8 is provided in accordance with necessity, and may be omitted.

An auxiliary passage open/close valve 8c for opening and closing the auxiliary passage 8 is provided at a midway point on the auxiliary passage 8. Further, an auxiliary passage open/close valve storage chamber 8d for storing the auxiliary passage open/close valve 8c so that the auxiliary passage open/close valve 8c is free to advance and retreat is provided at a midway point on the auxiliary passage 8. The auxiliary passage open/close valve 8c is stored so as to be free to advance to and retreat from a front portion side of the auxiliary passage open/close valve storage chamber 8d, or in other words so as to be free to move toward the upper portion side in FIGS. 1 to 9.

A spring 8e for biasing the auxiliary passage open/close valve 8c stored in the front portion side of the auxiliary passage open/close valve storage chamber 8d, or in other words the upper portion side in FIGS. 1 to 9, toward the front portion side (the upper portion side in FIGS. 1 to 9), i.e. in a direction for closing the auxiliary passage 8, is disposed on the rear portion side thereof, i.e. the lower portion side in FIGS. 1 to 9. Further, a spring pressure adjustment tool 8f for adjusting the spring pressure of the spring 8e is attached to the rear end side, i.e. the lower end side in FIGS. 1 to 9, of the auxiliary passage open/close valve storage chamber 8d.

The auxiliary passage open/close valve storage chamber 8d takes a cylindrical form, for example, with an auxiliary passage 8A and an auxiliary passage 8B opening onto the center of a front end surface thereof, i.e. the center of the upper end surface in FIGS, 1 to 9, and the side face of a front portion side thereof, i.e. the side face of the upper portion side in FIGS. 1 to 9, respectively. The auxiliary passage 8A opening onto the center of the front end surface communicates connectedly with a midway point on the bypass passage 75, while the auxiliary passage 8B opening onto the side face of the front portion side communicates connectedly with a midway point on the bending passage 74.

The auxiliary passage open/close valve 8c stored on the front portion side, i.e. the upper portion side in FIGS. 1 to 9, of the auxiliary passage open/close valve storage chamber 8d retreats (moves downward in FIGS. 1 to 9) when the internal pressure of the auxiliary passage 8A rises beyond a predetermined pressure, for example beyond a set pressure of the spring 8e, thereby opening the valve. On the other hand, the auxiliary passage open/close valve 8c does not open when the internal pressure of the bending passage 74 communicating with the auxiliary passage 8B on the side face of the front portion side (the upper portion side in FIGS. 1 to 9) of the auxiliary passage open/close valve storage chamber 8d rises. Further, a communicating passage 8g is provided between the side face of the rear portion side, i.e. the side face of the lower portion side in FIGS. 1 to 9, of the auxiliary passage open/close valve storage chamber 8d and the side face of the end portion side of the first cylinder chamber 71A.

Next, actions based on the structure of the embodiment of the present invention described above will be described.

When the thigh socket 2 of the prosthetic leg 1 is attached to the stump portion of the amputated leg and the foot portion 5 of the raised prosthetic leg 1 is moved forward of a healthy leg and then lowered until it contacts the ground such that body weight shifts to the prosthetic leg 1 side during walking on level ground, the heel 5b of the foot portion 5 contacts the ground followed by the toe 5a. As a result, a clockwise rotary moment centering on the virtual rotary center 61 of the buffer device 6 in FIG. 1 acts on the toe 5a due to the reactive force from the level ground surface, and by means of this rotary moment, the intermediate portion side 62b of the central base plate 62 of the buffer device 6 moves relatively toward the rear portion link plate 64 side.

At the same time, the diagonally upward-inclined tip end side of the central base plate 62 also moves relatively toward the rear portion link plate 64 side, whereby the connecting shaft 62a attached to the side face on the tip end side thereof moves toward the rear portion link plate 64 side within the elongated hole 79b of the grounding detection member 79 so as to contact the interior end portion of the elongated hole 79b near the rear portion link plate 64 side. Thus, the grounding detection member 79 is rotated upward, i.e. counter-clockwise in FIG. 1, about the pivot shaft 79a.

In FIG. 1, the grounding transmission member 78b, which is connected to the right end of the grounding detection member 79 rotating upward about the pivot shaft 79a, is pushed upward. When pushed upward, the grounding transmission member 78b pushes up the closing valve connecting/operating member 78, which is connected integrally to the upper portion thereof. The toe grounding closing valve 76, which is connected to the upper portion of the closing valve connecting/operating member 78 that has been pushed upward in FIG. 1, moves so as to close the bending passage 74. As a result, the bending passage 74 is locked such that the liquid in the second cylinder chamber 71B cannot move into the first cylinder chamber 71A through the bending passage 74.

When the prosthetic leg 1 is extended straight, the liquid in the second cylinder chamber 71B is capable of moving into the first cylinder chamber 71A through the bypass passage 75 and bending passage 74B until the prosthetic leg 1 bends to a small angle of approximately 20 or 30 degrees, for example, about the knee shaft 3, and therefore the piston 72 moves toward the second cylinder chamber 71B. Thus, even when the toe grounding closing valve 76 is locked, the movement of the piston 72 causes the piston rod 72a to contract slightly, enabling the prosthetic leg 1 to bend to a small angle of approximately 20 or 30 degrees, for example, about the knee shaft 3. When the prosthetic leg 1 bends to a small angle of approximately 20 or 30 degrees, for example, about the knee shaft 37 the sealing surface of the moving piston 72 passes one end of the bypass passage 75 that opens onto the side face of the cylinder chamber 71.

In this case, if the auxiliary passage 8A is provided, the internal pressure of the auxiliary passage 8 communicating with the bypass passage 75 increases while the prosthetic leg 1 bends to a small angle of approximately 20 or 30 degrees, for example, about the knee shaft 3 when, after the toe 5a of the foot portion 5 contacts the ground following grounding of the heel 5b, the operation to kick the ground surface back using the toe 5a continues such that the body is moved forward, and as the body moves forward, the knee shaft 3 of the prosthetic leg 1, the toe 5a of which has contacted the ground, performs a bending operation continuously.

When the increased internal pressure of the liquid increases beyond a predetermined internal pressure, the front end surface (the upper end surface in FIGS. 1 to 9) of the auxiliary passage open/close valve 8c is pushed thereby via the auxiliary passage 8A. The increased internal liquid pressure, which is higher than the predetermined pressure such that the front end surface (the upper end surface in FIGS. 1 to 9) of the auxiliary passage open/close valve 8c is pushed, is higher than the spring pressure of the spring 8e biasing the auxiliary passage open/close valve 8c, and therefore the auxiliary passage open/close valve 8c is caused to retreat (moved downward in FIGS. 1 to 9). When the front end surface (the upper end surface in FIGS. 1 to 9) of the retreating auxiliary passage open/close valve 8c retreats (moves downward in FIGS. 1 to 9) further than the auxiliary passage 8B on the side face of the front portion side (the upper portion side in FIGS. 1 to 9) of the auxiliary passage open/close valve storage chamber 8d, the auxiliary passage 8 opens. In other words, the auxiliary passage 8A and the auxiliary passage 8B enter a state of communication.

When the auxiliary passage 8 opens, the liquid in the bending passage 74 flows from the auxiliary passage 8B into the auxiliary passage 8A through the front side of the open auxiliary passage open/close valve 8c. The liquid then flows down the bypass passage 75, through the bending passage 74A, the open heel grounding closing valve 77, and the bending passage 74A, and into the first cylinder chamber 71A.

Thus, even after the side face of the piston 72 passes the inlet side of the bypass passage 75, the liquid in the second cylinder chamber 71B can flow into the first cylinder chamber 71A through the bending passage 74, auxiliary passage 8B, open auxiliary passage open/close valve 8c, auxiliary passage 8A, bypass passage 75, bending passage 74A, open heel grounding closing valve 77, and bending passage 74A, and as a result, the piston 72 can move in a direction for causing the piston rod 72a to contract, whereby the knee shaft 3 of the prosthetic leg 1 can bend continuously even after the bending angle exceeds a small angle of 20 or 30 degrees, for example. Thus, waling can be performed smoothly and continuously on level ground.

Further, when the thigh socket 2 of the prosthetic leg 1 is attached to the stump portion of the amputated leg in order to walk upstairs, whereby the toe 5a on the foot portion 5 of the raised prosthetic leg 1 lands on the next stair and contacts the ground such that body weight shifts to the prosthetic leg 1 side, a clockwise rotary moment centering on the virtual rotary center 61 of the buffer device 6 in FIG. 1 acts on the toe 5a due to reactive force from the ground contact surface of the stair, and as a result of this rotary moment, the intermediate portion side 62b of the central base plate 62 of the buffer device 6 moves relatively toward the rear portion link plate 64 side.

At the same time, the diagonally upward-inclined tip end side of the central base plate 62 also moves relatively toward the rear portion link plate 64 side, whereby the connecting shaft 62a attached to the side face on the tip end side thereof moves toward the rear portion side within the elongated hole 79b of the grounding detection member 79 so as to contact the interior front portion side end portion of the elongated hole 79b. Thus, the grounding detection member 79 is rotated upward, i.e. counter-clockwise in FIG. 1, about the pivot shaft 79a.

In FIG. 1, the grounding transmission member 78b, which is connected to the right end of the grounding detection member 79 rotating upward about the pivot shaft 79a, is pushed upward. When pushed upward, the grounding transmission member 7 8b pushes up the closing valve connecting/operating member 78, which is connected integrally to the upper portion thereof The toe grounding closing valve 76, which is connected to the upper portion of the closing valve connecting/operating member 78 that has been pushed upward in FIG. 1, moves so as to close the bending passage 74. As a result, the bending passage 74 is locked such that the liquid in the second cylinder chamber 71B cannot move into the first cylinder chamber 71A through the bending passage 74.

In this case, when the prosthetic leg 1 is extended straight, the liquid in the second cylinder chamber 71B is capable of moving into the first cylinder chamber 71A through the bypass passage 75, flow control valve 74c, and bending passage 74B until the prosthetic leg 1 bends to a small angle of approximately 20 or 30 degrees, for example, about the knee shaft 3, and therefore the piston 72 moves toward the second cylinder chamber 71B. Thus, even when the toe grounding closing valve 76 is locked, the movement of the piston 72 causes the piston rod 72a to contract slightly, enabling the prosthetic leg 1 to bend to a small angle of approximately 20 or 30 degrees, for example, about the knee shaft 3.

In this case, when the auxiliary passage 8 is provided and the prosthetic leg 1 bends to or above a small angle of approximately 20 or 30 degrees, for example, about the knee shaft 3, the sealing surface of the moving piston 72 passes one end of the bypass passage 75 that opens onto the side face of the cylinder chamber 71. Then, when the continuous bending operation of the knee shaft 3 of the prosthetic leg 1 is stopped or the knee shaft 3 is held in a bent state in advance, the liquid stops flowing into the bypass passage 75 such that the internal pressure of the auxiliary passage 8A falls below the spring pressure of the spring 8e. As a result, the auxiliary passage open/close valve 8c closes such that the toe grounding closing valve 76 enters a locked state, whereby movement of the liquid in the second cylinder chamber 713 into the first cylinder chamber 71A is completely halted. As a result, movement of the piston 72 into the second cylinder chamber 71B, or in other words bending of the knee of the prosthetic leg 1, is completely prevented, thereby preventing buckling of the knee.

When full body weight is applied to the prosthetic leg 1 while the knee is prevented from buckling, the healthy leg standing on the lower stair is raised so as to contact the stair above the stair on which the prosthetic leg 1 is standing. Full body weight is then applied to the healthy leg, whereupon the prosthetic leg 1 is raised such that the toe 5a on the foot portion 5 of the prosthetic leg 1 contacts the stair above the stair on which the healthy leg is standing. By repeating a similar operation alternately, stairs can be ascended smoothly with similar leg movements to those of a healthy person without buckling of the knee of the prosthetic leg 1.

When descending stairs, on the other hand, the heel 5b on the foot portion 5 of the raised prosthetic leg 1 is lowered so as to contact the lower stair such that body weight shifts to the prosthetic leg 1 side. As a result, a counter-clockwise rotary moment centering on the virtual rotary center 61 of the buffer device 6 in FIG. 2 acts on the heel 5b due to reactive force from the contact surface of the stair, and by means of this rotary moment, the intermediate portion side 62b of the central base plate 62 of the buffer device 6 moves relatively toward the front portion link plate 63 side.

At the same time, the diagonally upward-inclined tip end side of the central base plate 62 also moves relatively toward the front portion side, whereby the connecting shaft 62a attached to the side face on the tip end side thereof moves toward the front portion side within the elongated hole 79b of the grounding detection member 79 so as to contact the interior front portion side end portion of the elongated hole 79b. Thus, the grounding detection member 79 is rotated downward, i.e. clockwise in FIG. 1, about the pivot shaft 79a.

In FIG. 1, the grounding transmission member 78b, which is connected to the right end of the grounding detection member 79 rotating downward about the pivot shaft 79a, is pulled downward. When pulled downward, the grounding transmission member 78b pulls down the closing valve connecting/operating member 78, which is connected integrally to the upper portion thereof. The heel grounding closing valve 77, which is connected to the lower portion of the closing valve connecting/operating member 78 that has been pulled downward in FIG. 2, moves so as to close the bending passage 74A. As a result, the bending passage 74A is locked so that the liquid in the second cylinder chamber 71B moves into the first cylinder chamber 71A through the flow control valve 74c and the bending passage 74B.

When the bending passage 74A is locked by the heel grounding closing valve 77, the liquid in the second cylinder chamber 71B passes through the flow control valve 74c for limiting the flow rate thereof, and therefore the movement resistance of the piston 72 to the second cylinder chamber 71B side increases, or in other words the bending resistance of the prosthetic leg 1 increases, such that the prosthetic leg 1 bends slowly, thereby preventing sudden buckling of the knee. Even when heel grounding switches to toe grounding while the knee bends slowly, the heel grounding closing valve 77 remains closed due to the high internal pressure of the liquid.

With full body weight applied to the prosthetic leg 1, the knee of which bends slowly, the healthy leg standing on the upper stair is pulled downward. Meanwhile, the knee of the prosthetic leg 1 bends slowly. After the healthy leg has contacted the stair below the stair on which the prosthetic leg 1 is standing, full body weight is applied to the healthy leg and the prosthetic leg 1 is pulled downward such that the heel 5b on the foot portion 5 of the prosthetic leg 1 contacts the stair below the stair on which the healthy leg is standing. By repeating a similar operation alternately, stairs can be descended smoothly with similar leg movements to those of a healthy person without buckling of the knee of the prosthetic leg 1.

Meanwhile, when the bent k nee of the prosthetic leg 1 is extended, the extension passage 73 bears no relationship to the toe grounding closing valve 76 and the heel grounding closing valve 77, even when the toe grounding closing valve 76 or the heel grounding closing valve 77 performs locking, and therefore, even when the toe 5a or the heel 5b of the foot portion 5 is grounded, the liquid in the first cylinder chamber 71A can move to the second cylinder chamber 71B side through the extension passage 73. Thus, the bent prosthetic leg 1 can be extended.

Figure 10:
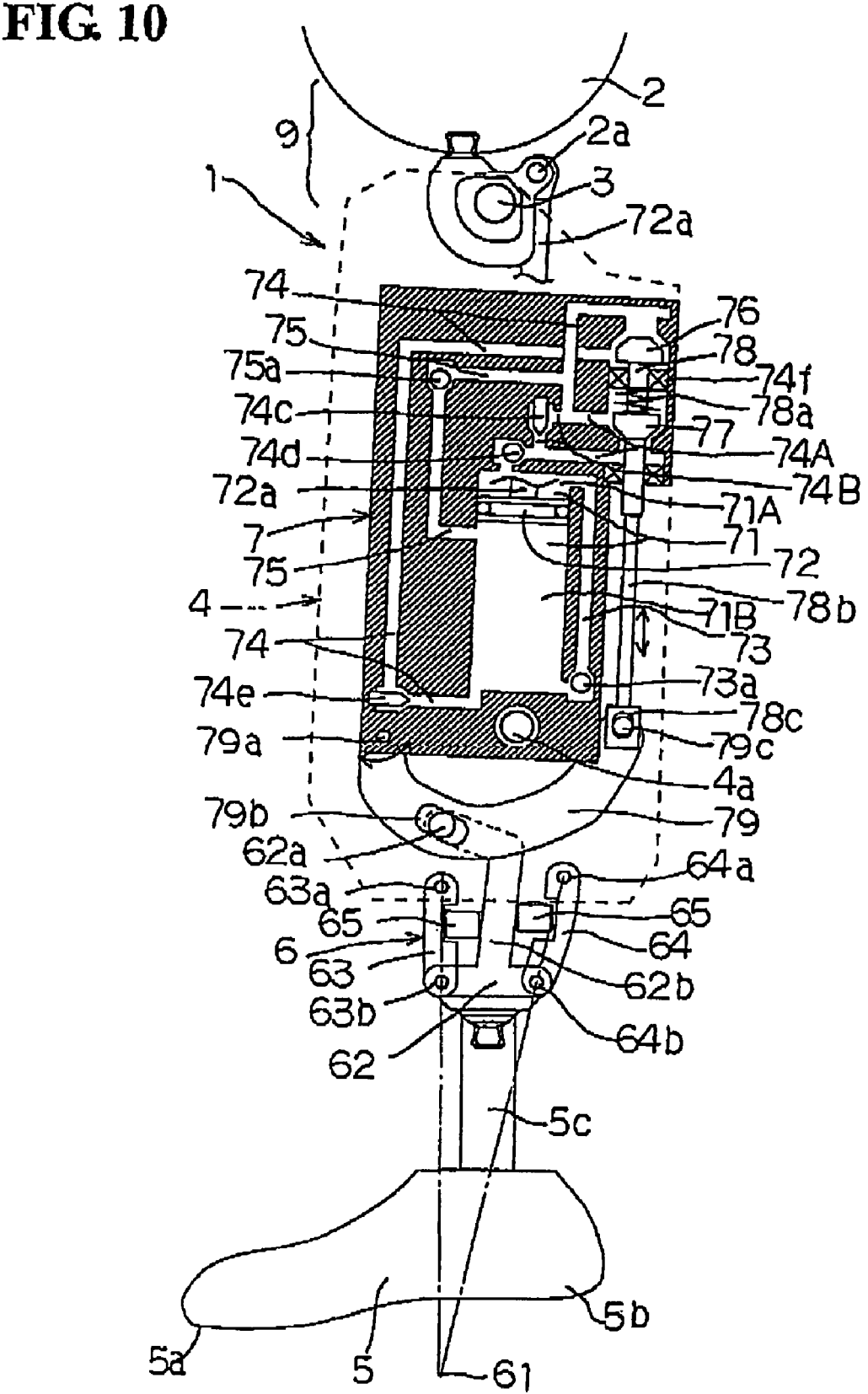
FIG. 10 is a side sectional view showing the main parts of a prosthetic leg not having an auxiliary passage in a neutral state, according to another embodiment of the present invention.

Note that the present invention is not limited to the embodiment described above, and may of course be subjected to various improvements within a scope that does not depart from the spirit of the present invention For example, in the embodiment described above, the auxiliary passage 8 is provided, but, as shown in FIG. 10, the auxiliary passage 8 may be omitted if necessary.

What is claimed is:

1. A prosthetic leg which is configured to be attached to a leg that has been amputated proximal to the knee as a substitute leg, and which is installed with a hydraulic cylinder for adjusting bending and extension resistance of a knee joint portion, wherein, when a piston provided in a cylinder chamber of the hydraulic cylinder moves in a direction for extending the prosthetic leg, an extension passage allows passage of a liquid in a first cylinder chamber into a second cylinder chamber, and when the piston provided in the cylinder chamber of the hydraulic cylinder moves in a direction for bending the prosthetic leg, a bending passage allows passage of the liquid in the second cylinder chamber into the first cylinder chamber, the bending passage bifurcates into two at a midway point thereon so as to connect to the first cylinder chamber side, a toe grounding closing valve being provided at a midway point on the bending passage prior to bifurcation for closing the bending passage when a toe on a foot portion of the prosthetic leg contacts the ground and a heel grounding closing valve being provided at a midway point on one of the bending passages following bifurcation for closing the bending passage when a heel on the foot portion of the prosthetic leg contacts the ground, and the toe grounding closing valve and the heel grounding closing valve are connected by a closing valve connecting/operating member for connecting the toe grounding closing valve and the heel grounding closing valve in an interlocking manner such that valve open/close orientations thereof are set in opposite directions.

2. The prosthetic leg according to claim 1, wherein a bypass passage is provided for allowing the passage of the liquid in the second cylinder chamber toward the first cylinder chamber until the piston moves in a direction for bending the prosthetic leg, the knee of which is extended, to a small angle,
   one end of the bypass passage is openly connected to an intermediate site on an interior side face of the cylinder chamber, and
   the other end of the bypass passage is connected to the bending passage on a downstream side of the toe grounding closing valve.

3. The prosthetic leg according to claim 1, wherein an auxiliary passage is provided between the bending passage on an upstream side of the toe grounding closing valve and the bypass passage, and an auxiliary passage open/close valve is provided for opening the auxiliary passage when an internal pressure of the bypass passage increases beyond a predetermined internal pressure.

4. A prosthetic leg which is configured to be attached to a leg that has been amputated proximal to the knee as a substitute leg, and which is installed with a hydraulic cylinder for adjusting bending and extension resistance of a knee joint portion,
   wherein a buffer device is provided between a lower leg portion and a foot portion below the knee joint portion for displacing movably in opposite directions when a toe of the foot portion and a heel of the foot portion contact the ground, respectively,
   when a piston provided in a cylinder chamber of the hydraulic cylinder moves in a direction for extending the prosthetic leg, an extension passage allows passage of a liquid in a first cylinder chamber into a second cylinder chamber, and when the piston provided in the cylinder chamber of the hydraulic cylinder moves in a direction for bending the prosthetic leg, a bending passage allows passage of the liquid in the second cylinder chamber into the first cylinder chamber,
   the bending passage bifurcates into two at a midway point thereon so as to connect to the first cylinder chamber side, a toe grounding closing valve being provided at a midway point on the bending passage prior to bifurcation for closing the bending passage when the toe on the foot portion of the prosthetic leg contacts the ground and a heel grounding closing valve being provided at a midway point on one of the bending passages following bifurcation for closing the bending passage when the heel on the foot portion of the prosthetic leg contacts the ground,
   the toe grounding closing valve and the heel grounding closing valve are connected by a closing valve connecting/operating member for connecting the toe grounding closing valve and the heel grounding closing valve in an interlocking manner such that valve open/close orientations thereof are set in opposite directions,
   a grounding detection member is provided for detecting movable displacement of the buffer device when the toe or the heel on the foot portion of the prosthetic leg contacts the ground,
   a grounding transmission member is provided for transmitting movable displacement of the grounding detection member to the closing valve connecting/operating member to make the closing valve connecting/operating member movable, and
   the movable displacement of the grounding detection member caused by grounding of the toe on the foot portion of the prosthetic leg is transmitted by the grounding transmission member to operate the toe grounding closing valve connected to the closing valve connecting/operating member in a closing direction and operate the heel grounding closing valve in an opening direction, and the movable displacement of the grounding detection member caused by grounding of the heel on the foot portion of the prosthetic leg is transmitted by the grounding transmission member to operate the heel grounding closing valve connected to the closing valve connecting/operating member in a closing direction and operate the toe grounding closing valve in an opening direction.

5. The prosthetic leg according to claim 4, wherein a bypass passage is provided for allowing the passage of the liquid in the second cylinder chamber toward the first cylinder chamber until the piston moves in a direction for bending the prosthetic leg, the knee of which is extended, to a small angle,
   one end of the bypass passage is openly connected to an intermediate site on an interior side face of the cylinder chamber, and
   the other end of the bypass passage is connected to the bending passage on a downstream side of the toe grounding closing valve.

6. The prosthetic leg according to claim 4, wherein an auxiliary passage is provided between the bending passage on an upstream side of the toe grounding closing valve and the bypass passage, and an auxiliary passage open/close valve is provided for opening the auxiliary passage when an internal pressure of the bypass passage increases beyond a predetermined internal pressure.

* * * * *